(12) United States Patent  
Tian

(10) Patent No.: US 10,006,899 B2  
(45) Date of Patent: Jun. 26, 2018

(54) NANOPORE-BASED SEQUENCING CHIPS USING STACKED WAFER TECHNOLOGY

(71) Applicant: Genia Technologies, Inc., Mountain View, CA (US)

(72) Inventor: Hui Tian, Cupertino, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 842 days.

(21) Appl. No.: 14/225,263

(22) Filed: Mar. 25, 2014

(65) Prior Publication Data

US 2015/0275287 A1    Oct. 1, 2015

(51) Int. Cl.
*C12Q 1/68*    (2018.01)
*G01N 33/487*    (2006.01)

(52) U.S. Cl.
CPC .............. *G01N 33/48721* (2013.01)

(58) Field of Classification Search
CPC ............. G01N 33/48721; G01N 33/68; G01N 27/44791; G01N 27/4473; Y10S 977/852; Y10S 977/733; Y10S 977/72; Y10S 977/721; C12Q 1/6813; C12Q 1/6876; C12Q 1/6825; C12Q 1/6869
See application file for complete search history.

(56) References Cited

U.S. PATENT DOCUMENTS

| | | | |
|---|---|---|---|
| 7,052,941 B2 | 5/2006 | Lee | |
| 2005/0282356 A1* | 12/2005 | Lee | H01L 21/2007 438/458 |
| 2009/0027143 A1* | 1/2009 | Jensen | H01P 11/003 333/238 |
| 2009/0136958 A1* | 5/2009 | Gershow | C12Q 1/6825 435/6.13 |
| 2009/0150084 A1 | 6/2009 | Colwell et al. | |
| 2010/0292101 A1 | 11/2010 | Wai-Cheong | |
| 2011/0133255 A1 | 6/2011 | Merz | |
| 2011/0147895 A1 | 6/2011 | Bai | |
| 2011/0193570 A1* | 8/2011 | Chen | C12Q 1/6816 324/654 |
| 2012/0060589 A1 | 3/2012 | Gridelet | |
| 2012/0197623 A1* | 8/2012 | Homer | C12Q 1/6869 703/11 |
| 2013/0056862 A1 | 3/2013 | Kim | |

(Continued)

FOREIGN PATENT DOCUMENTS

| | | |
|---|---|---|
| WO | PCT-2005004197 | 1/2005 |
| WO | PCT-2008076406 | 6/2008 |

(Continued)

*Primary Examiner* — Gurpreet Kaur
(74) *Attorney, Agent, or Firm* — Van Pelt, Yi & James LLP

(57) ABSTRACT

A nanopore based sequencing chip is disclosed. The sequencing chip comprises a first portion made from a first wafer. The first portion includes an array of nanopore cells. The first portion further includes a measurement circuit connected to one or more nanopore cells, the measurement circuit producing an output measurement signal. The first portion further includes one or more vias transmitting the output measurement signal. The sequencing chip further includes a second portion made from a second wafer, the second portion comprising one or more corresponding vias receiving the output measurement signal.

12 Claims, 14 Drawing Sheets

(56) References Cited

U.S. PATENT DOCUMENTS

| | | | |
|---|---|---|---|
| 2013/0207205 A1* | 8/2013 | Chen | H01L 23/552 |
| | | | 257/414 |
| 2013/0240378 A1 | 9/2013 | Lee | |
| 2013/0292743 A1 | 11/2013 | Rothberg et al. | |
| 2014/0329693 A1* | 11/2014 | Reid | G01N 33/48721 |
| | | | 506/2 |

FOREIGN PATENT DOCUMENTS

| | | |
|---|---|---|
| WO | PCT-2010132603 | 11/2010 |
| WO | WO-2011097028 | 8/2011 |

* cited by examiner

നാനോPORE-BASED SEQUENCING CHIPS
USING STACKED WAFER TECHNOLOGY

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
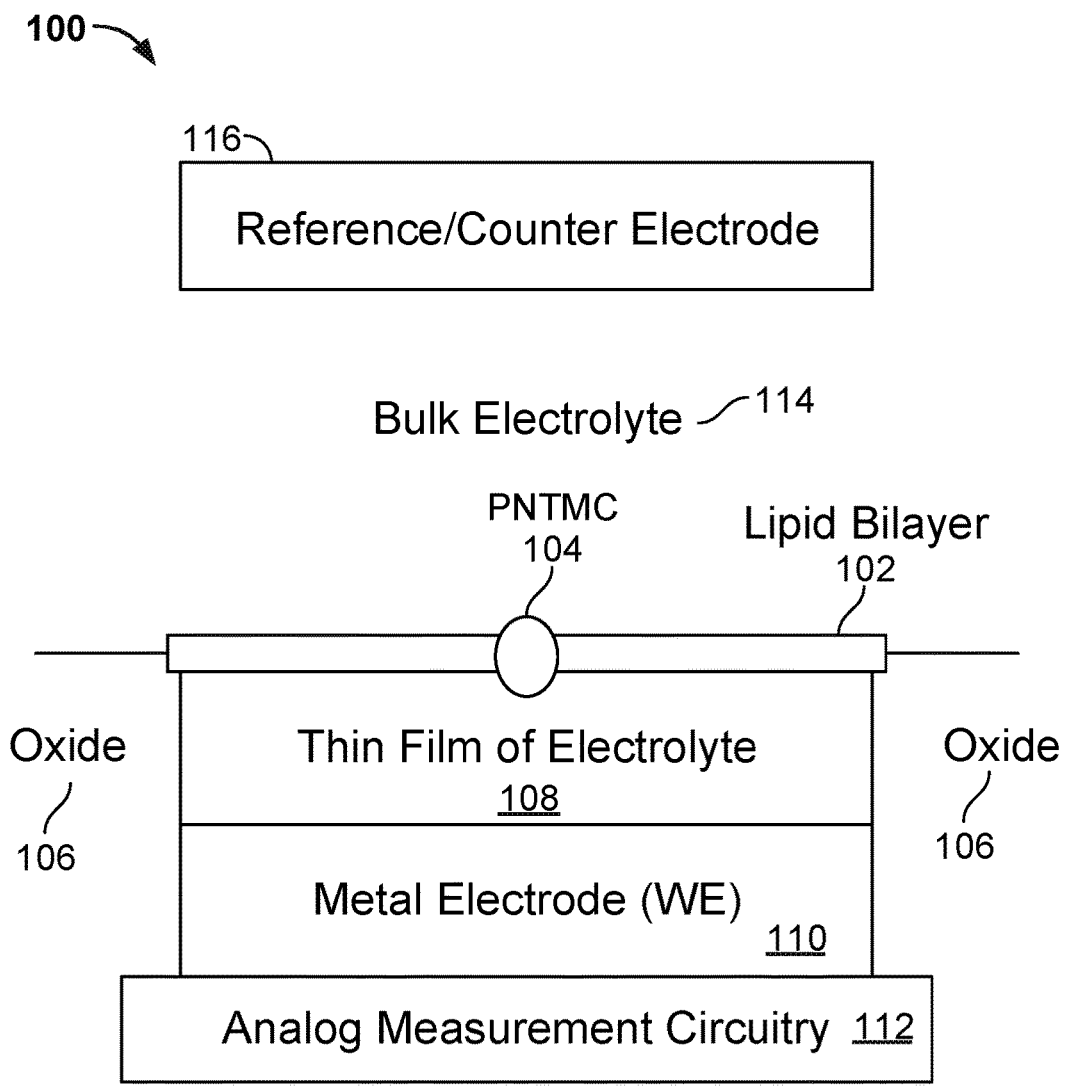
FIG. 1 illustrates an embodiment of a cell 100 in a nanopore based sequencing chip.

FIG. 1 illustrates an embodiment of a cell 100 in a nanopore based sequencing chip. A lipid bilayer 102 is formed over the surface of the cell. The bulk electrolyte 114 containing soluble protein nanopore transmembrane molecular complexes (PNTMC) and the analyte of interest is placed directly onto the surface of the cell. A single PNTMC 104 is inserted into lipid bilayer 102 by electroporation. The individual lipid bilayers in the array are not connected to each other either chemically or electrically. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable lipid bilayer 102. PNTMC 104 crosses lipid bilayer 102 and provides the only path for ionic current to flow from the bulk liquid to metal electrode 110. Metal electrode 110 is also referred to as the working electrode (WE). The cell also includes a counter/reference electrode (CE/RE) 116, which is an electrochemical potential sensor.

Figure 2:
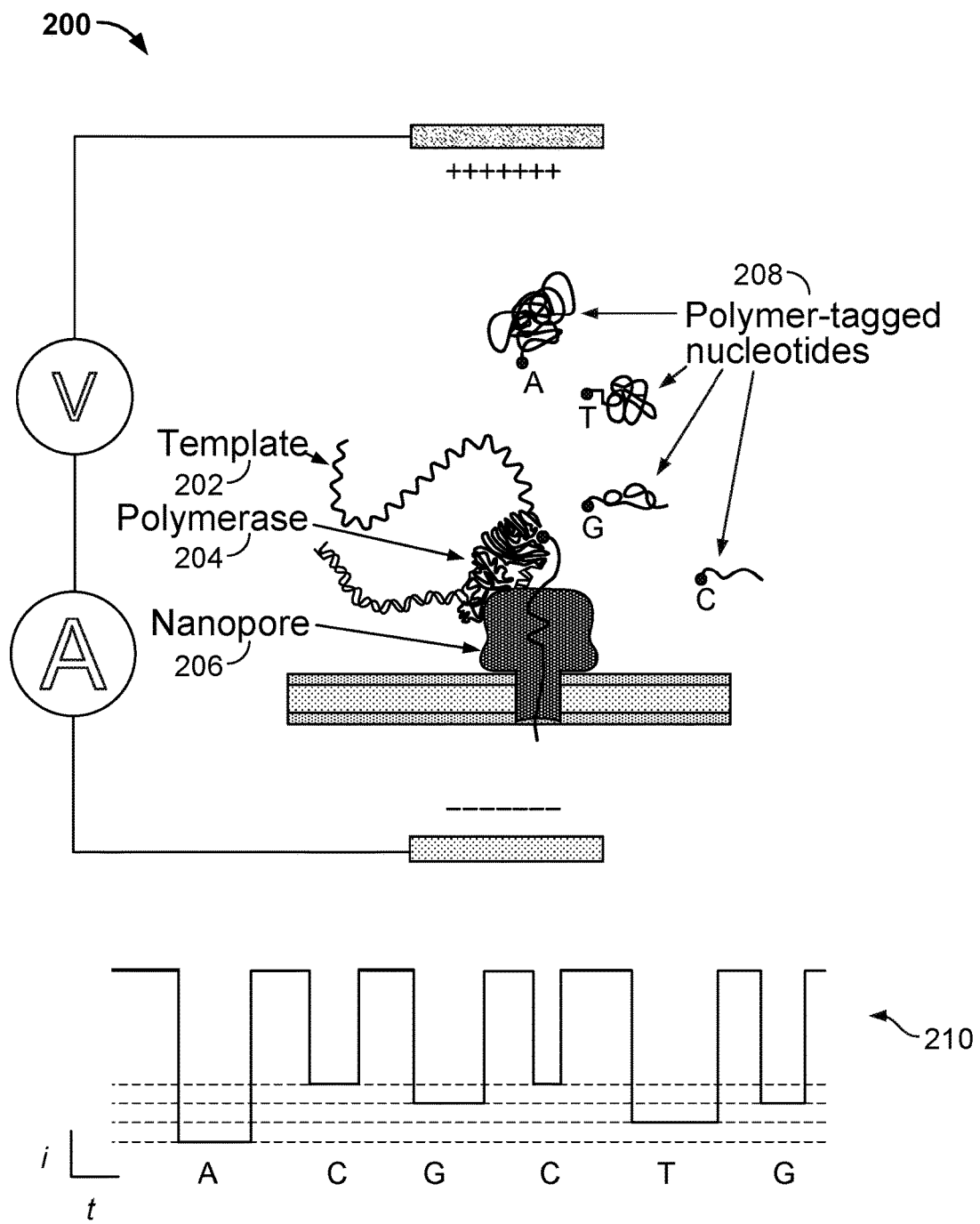
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. After polymerase catalyzed incorporation of the correct nucleotide, the tag-attached polyphosphate held in the barrel of nanopore 206 generates a unique ionic current blockade signal 210, thereby identifying the added base electronically due to the tags' distinct chemical structures.

Figure 3:
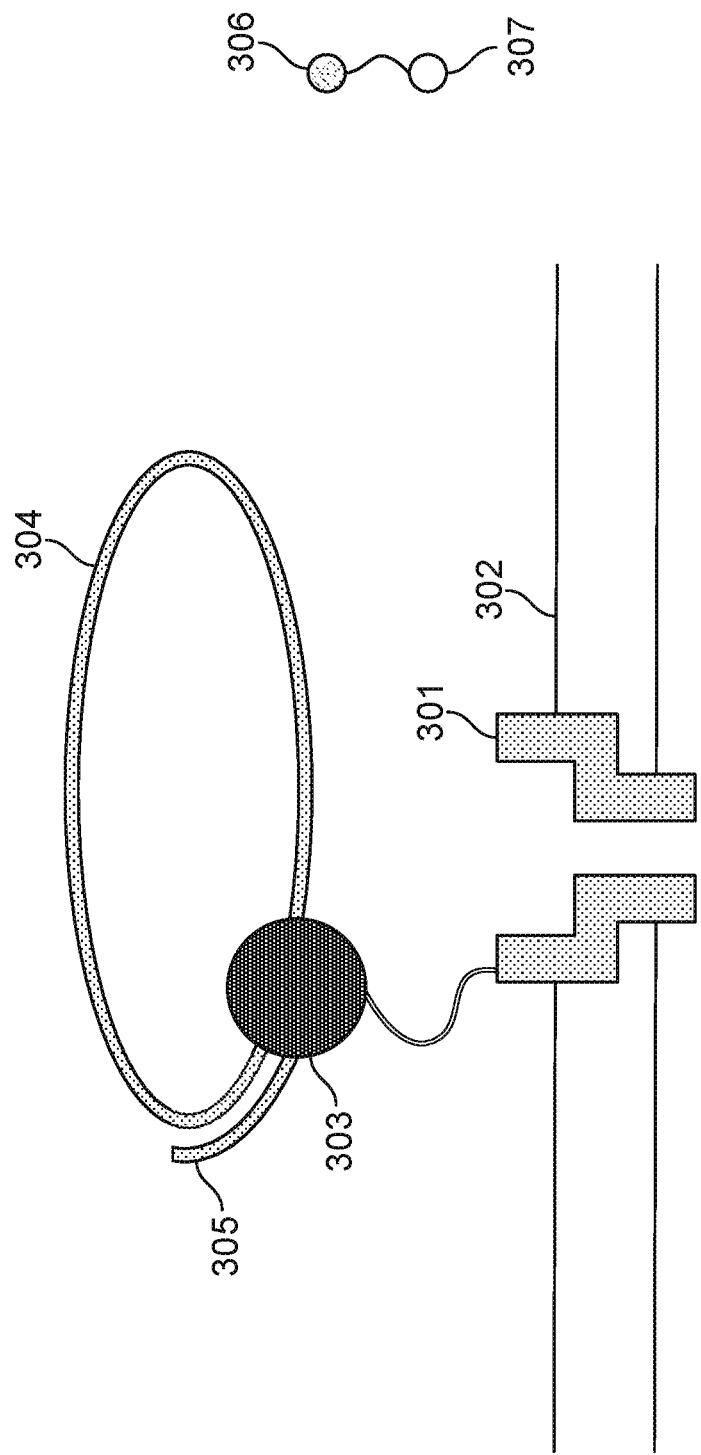
FIG. 3 illustrates an embodiment of a cell performing nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a single stranded nucleic acid molecule 304 to be sequenced. In some embodiments, single or double stranded nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
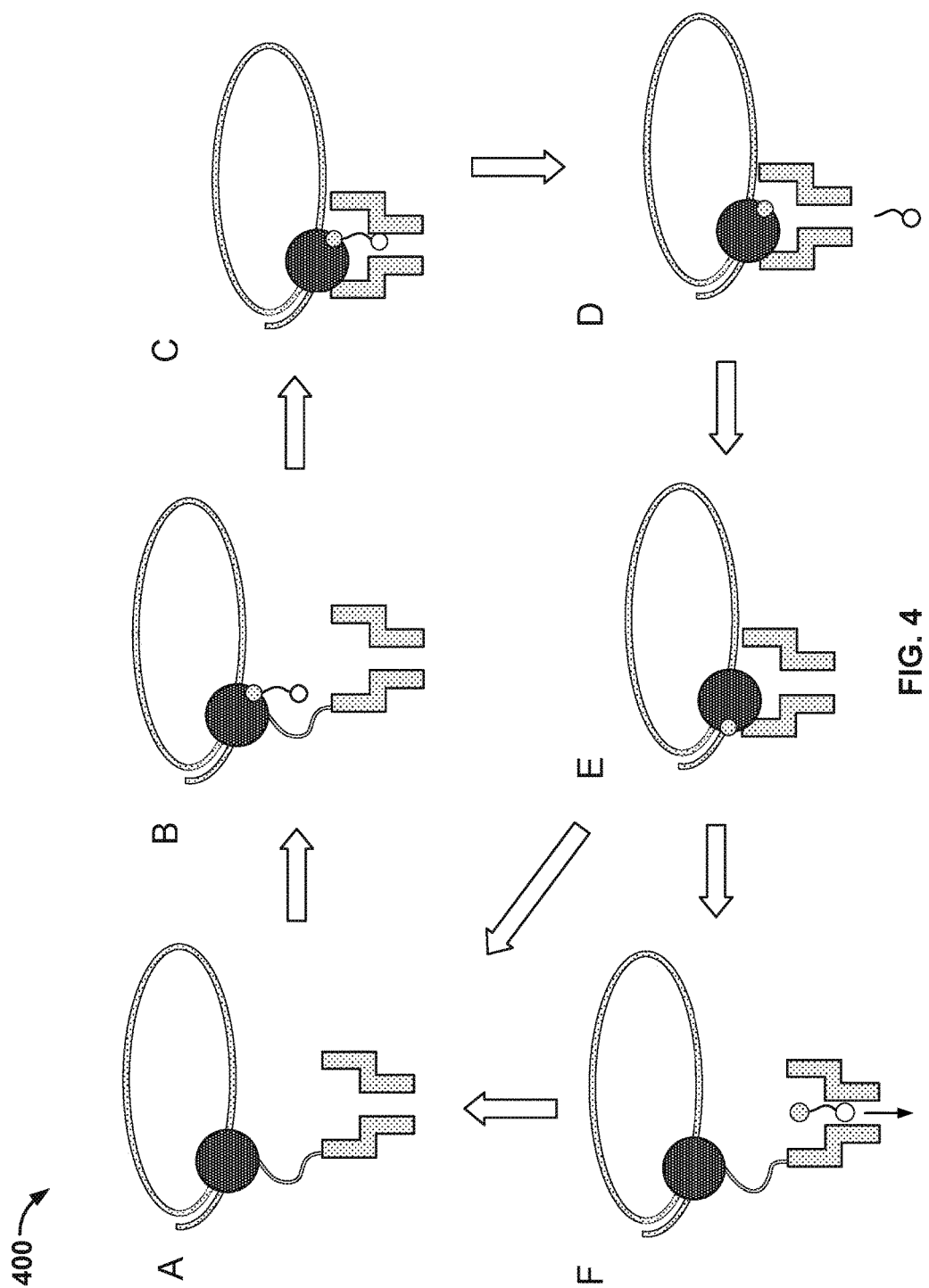
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 1000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are base paired with the single stranded nucleic acid molecule (e.g., A with T and G with C). However, some of the associated tagged nucleotides are not base paired with the single stranded nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the current passing through the nanopore is ~30 picoamps (pA). At stage C, the current flowing through the nanopore is about 6 pA, 8 pA, 10 pA, or 12 pA, each amperage corresponding to one of the four types of tagged nucleotides. The polymerase undergoes an isomerization and a transphosphorylation reaction to incorporate the nucleotide into the growing nucleic acid molecule and release the tag molecule. At stage D, the released tag passes through the nanopore. The tag is detected by the nanopore. In particular, as the tag is held in the nanopore, a unique ionic current blockade signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

In some embodiments, the ionic current (e.g., see signal 210 in FIG. 2) is read by analog measurement circuit 112 (see FIG. 1) in each cell, converted to digital information and transmitted out of the chip. In some embodiments, a field programmable gate array (FPGA) or application-specific integrated circuit (ASIC) receives the transmitted data, processes the data, and forwards the data to a computer. However, as the nanopore based sequencing chip is scaled to include more and more cells, the aggregate transmission data rate to and from the nanopore based sequencing chip may increase to an unattainable rate. For example, a nanopore based sequencing chip with 128 k cells may require sixteen channels at one gigabits per second each, while a chip with one million, ten million, or one hundred million cells may require 160 channels, 1,600 channels, or 16,000 channels at one gigabits per second per channel, respectively.

The aggregate transmission data rate of the nanopore based sequencing chip may be reduced by a number of ways. In some embodiments, digital compression techniques may be used to compress some of the data on the nanopore based sequencing chip, and then the compressed data may be transmitted out of the chip at a lower transmission rate. In some embodiments, some of the data may be processed (e.g., using base-calling techniques) on the nanopore based sequencing chip. The processed data may be transmitted out of the chip, e.g., to a computer for further processing. Alternatively, the processed data may be used by the nanopore based sequencing chip for detecting events and generating control signals in response to the detected events. The generated control signals may be fed back into the individual cells or groups of cells as input control signals. Because some of the detections and decisions are made on-chip, less data is required to be transmitted out of the chip for further processing and less control data may be transmitted to the chip, and the response time for generating the control data may also be reduced.

As shown above, as the nanopore based sequencing chip scales to include more cells, the chip may include different types of components, e.g., analog, digital, and memory components. The different types of components may be partitioned into two or more wafers that are stacked vertically to form a stacked-wafers nanopore based sequencing chip. For example, each stacked wafer includes a different type of components, e.g., analog components only and digital components only. One advantage of separating digital components and analog components into different wafers is that it eliminates the need for mixed-signal wafers on the chip, which are more expensive than analog wafers or digital wafers that can be individually designed with different types of technologies, e.g., 180 nm technology for analog design and 28 nm technology for digital design.

Figure 5A:
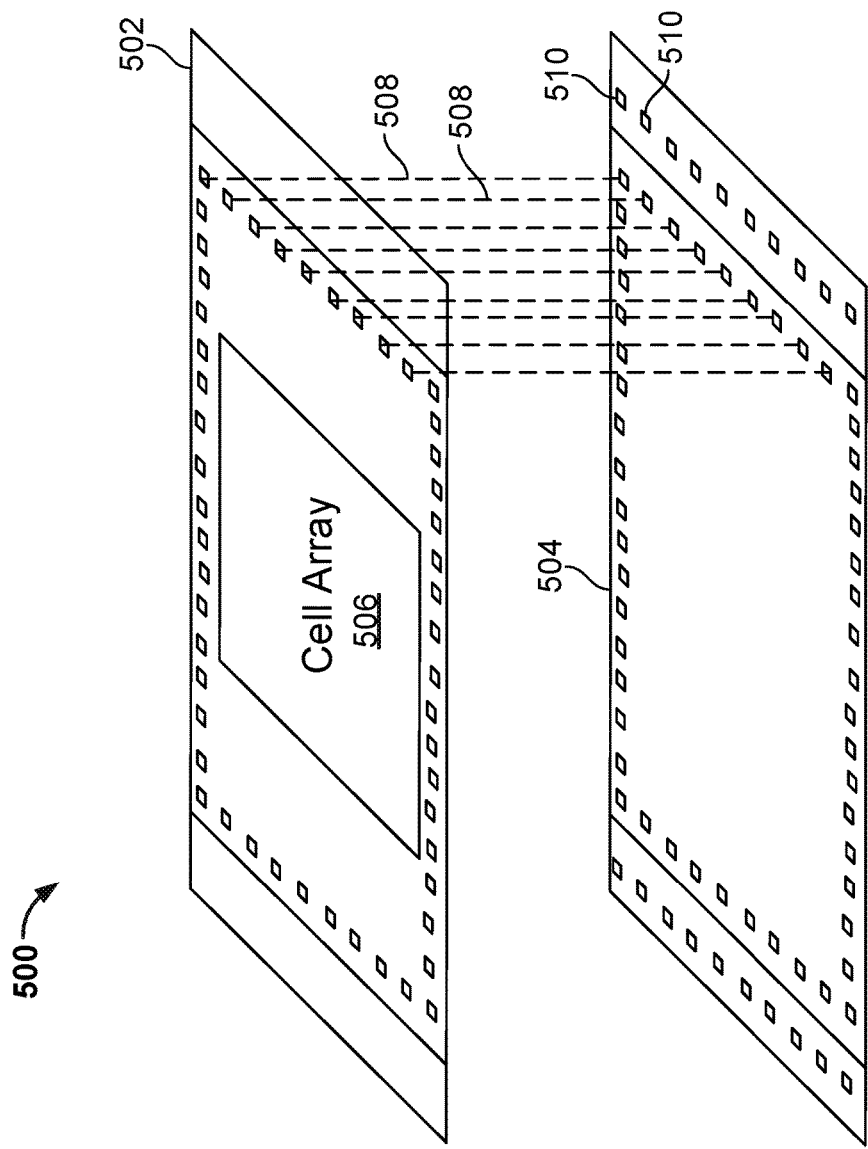
FIG. 5A illustrates an embodiment of a stacked-wafers nanopore based sequencing chip 500 that includes two separate wafers (502 and 504).
Figure 5B:
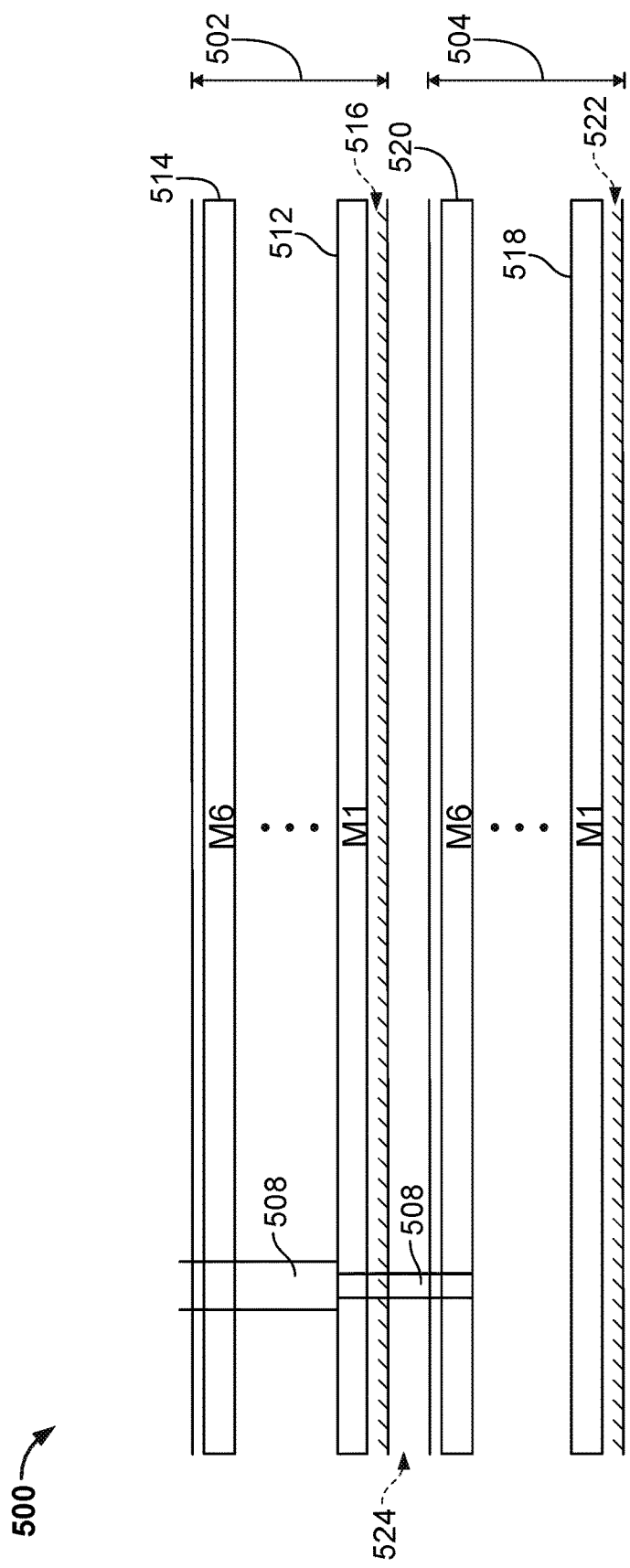
FIG. 5B illustrates the cross-sectional view of stacked-wafers nanopore-based sequencing chip 500.

FIG. 5A illustrates an embodiment of a stacked-wafers nanopore based sequencing chip 500 that includes two portions that are made from two separate wafers (502 and 504). In FIG. 5A, the top wafer 502 and the bottom wafer 504 are shown as two separate wafers. FIG. 5B illustrates the cross-sectional view of stacked-wafers nanopore-based sequencing chip 500. As shown in FIG. 5B, top wafer 502 is stacked vertically on top of bottom wafer 504.

With reference to FIG. 5A, top wafer 502 includes a nanopore cell array 506. Nanopore cell array 506 may include a large number of sensor cells configured as an array. For example, an array of one million cells may include 1000 rows by 1000 columns of cells.

Top wafer 502 includes nanopore cell array 506, including each cell's corresponding analog measurement circuits (e.g., see analog measurement circuitries 112). In some embodiments, the analog circuits may be designed in 180 nm technology. In some embodiments, analog signals from individual cells are routed from the cells to analog-to-digital converters (ADCs) where the analog signals are converted into corresponding digital signals. The digital signals are further routed to the periphery of top wafer 502 and transmitted through a plurality of vias 508 (e.g., through-silicon vias (TSVs)) to the periphery of bottom wafer 504. A via is an electric connection between layers in a physical electronic circuit that goes through the plane of one or more adjacent layers. In some embodiments, a via 508 may have a diameter of 4 μm. Placing the vias along the periphery of the top wafer and the bottom wafer is also referred to as periperhal stacking.

Bottom wafer 504 includes digital logic circuits. In some embodiments, the digital circuits may be designed in 28 nm technology. In some embodiments, some of the signals transmitted from top wafer 502 may be transmitted out of nanopore-based sequencing chip 500 through a plurality of input/output (I/O) pads 510 without further processing by bottom wafer 504. Some of the signals transmitted from top wafer 502 may be further processed or compressed by logic located on bottom wafer 504. The processed data is then transmitted out of nanopore-based sequencing chip 500, e.g., to a computer or a piece of hardware, for further processing. Alternatively, the processed data may be used by nanopore based sequencing chip 500 for detecting events and generating control signals in response to the detected events. The generated control signals may be sent through a plurality of vias 508 to top wafer 502 and then fed back into the individual cells or groups of cells as input control signals. Signals may be transmitted from a computer or a source outside nanopore-based sequencing chip 500 to bottom wafer 504 through I/O pads 510. These signals may be used as input or control signals for controlling any logic or circuits on top wafer 502 or bottom wafer 504. For the former case, the signals are directed through vias 508 to top wafer 502 and then routed to specific regions, specific cells, or specific groups of cells.

In some embodiments, each ADC may be divided into two portions: one portion of the ADC is located on top wafer 502, and the remaining portion of the ADC is located on bottom wafer 504.

With reference to FIG. 5B, top wafer 502 is stacked vertically on top of bottom wafer 504, with a layer of oxide 524 bonding the two wafers together. In some embodiments, top wafer 502 and bottom wafer 504 each includes a plurality of metal layers, M1 (512) to M6 (514) and a layer of silicon oxide (516 and 522). Vias 508 provide an electric connection between the metal layers. Signals are transmitted between top wafer 502 and bottom wafer 504 through vias 508. In some embodiments, vias 508 are filled with tungsten.

Figure 6:
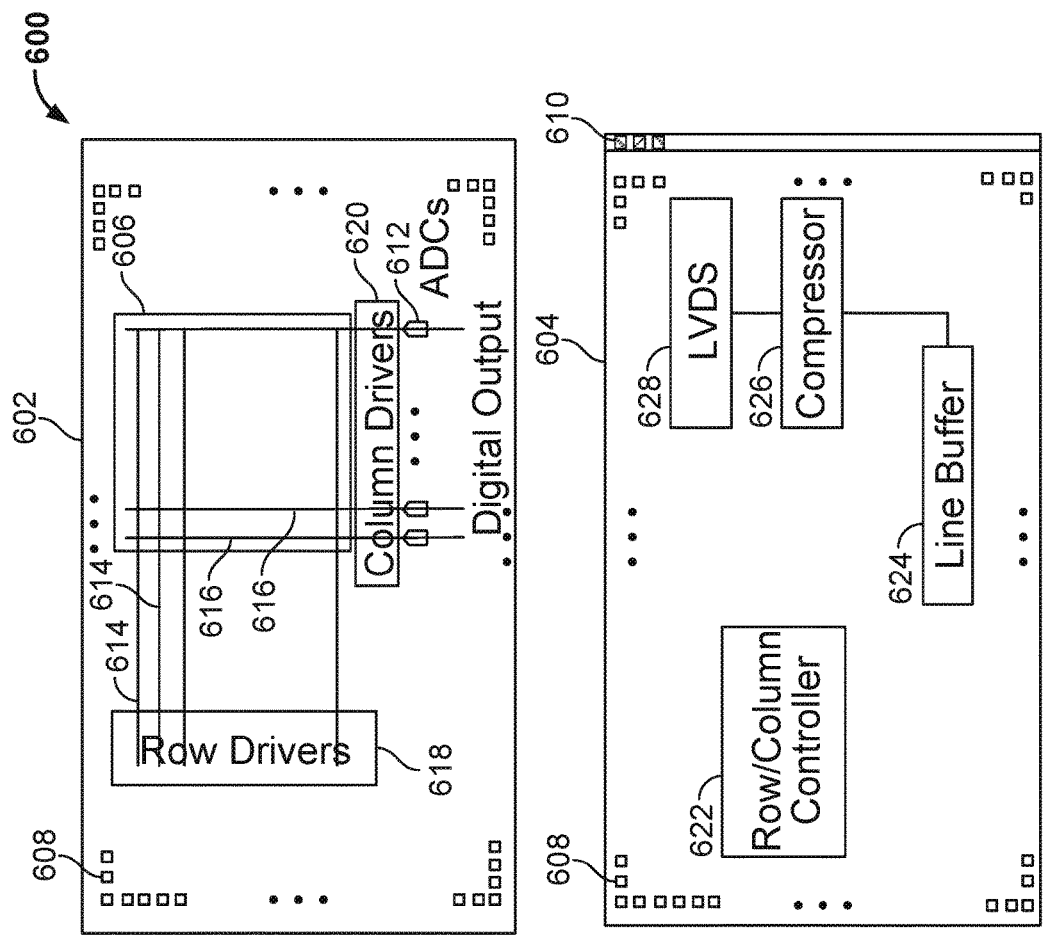
FIG. 6 illustrates an embodiment of a stacked-wafers nanopore based sequencing chip 600 that includes two separate wafers, a top wafer 602 and a bottom wafer 604.

FIG. 6 illustrates an embodiment of a stacked-wafers nanopore based sequencing chip 600 that includes two separate wafers, a top wafer 602 and a bottom wafer 604. Top wafer 602 includes a nanopore cell array 606. In this embodiment, vias 608 are placed at the periphery of the wafers. Bottom wafer 604 includes I/O pads 610.

Signals may be transmitted from a computer or a source outside nanopore-based sequencing chip 600 to bottom wafer 604 through I/O pads 610. These signals may be used as input or control signals for controlling any logic or circuits on top wafer 602 or bottom wafer 604. Examples of this type of signals include power and ground signals. Power and ground signals are directed through vias 608 to top wafer 602 and then routed to specific regions, specific cells, or specific groups of cells.

Some signals that are transmitted through vias 608 include output signals from nanopore cell array 606. Analog signals from individual cells are routed from the cells to analog-to-digital converters (ADCs) 612 where the analog signals are converted into corresponding digital signals. The digital signals are further routed to the periphery of top wafer 602 and transmitted through a plurality of vias 608 to the periphery of bottom wafer 604. The digital signals may be received and saved by a frame buffer 624. Some of the digital signals may be further sent to different modules (e.g., compressor 626 and low-voltage differential signaling (LVDS) module 628) for further processing.

In some embodiments, each ADC 612 is shared between different rows 614 and/or different columns 616 of cells in nanopore cell array 616. Row and column controller 622 on bottom wafer 604 sends control information to row and column drivers (618 and 620), which in turn drive the output signals corresponding to different rows and columns of the nanopore cells in nanopore cell array 606 onto their corresponding ADCs 612.

Some signals that are transmitted through vias 608 include signals that are routed into a specific nanopore cell as input signals or control signals that control the individual cell. The input or control signals may be generated by modules on bottom wafer 604 in response to certain detected events. The input or control signals may be generated by a computer or a piece of hardware outside nanopore-based sequencing chip 600 in response to certain detected events. Examples of these types of signals include signals known as seta, setb, $V_A$, $V_B$, row select, and reset, as will be described in greater detail below (see e.g., FIG. 7B, FIG. 11, and FIG. 12).

Figure 7A:
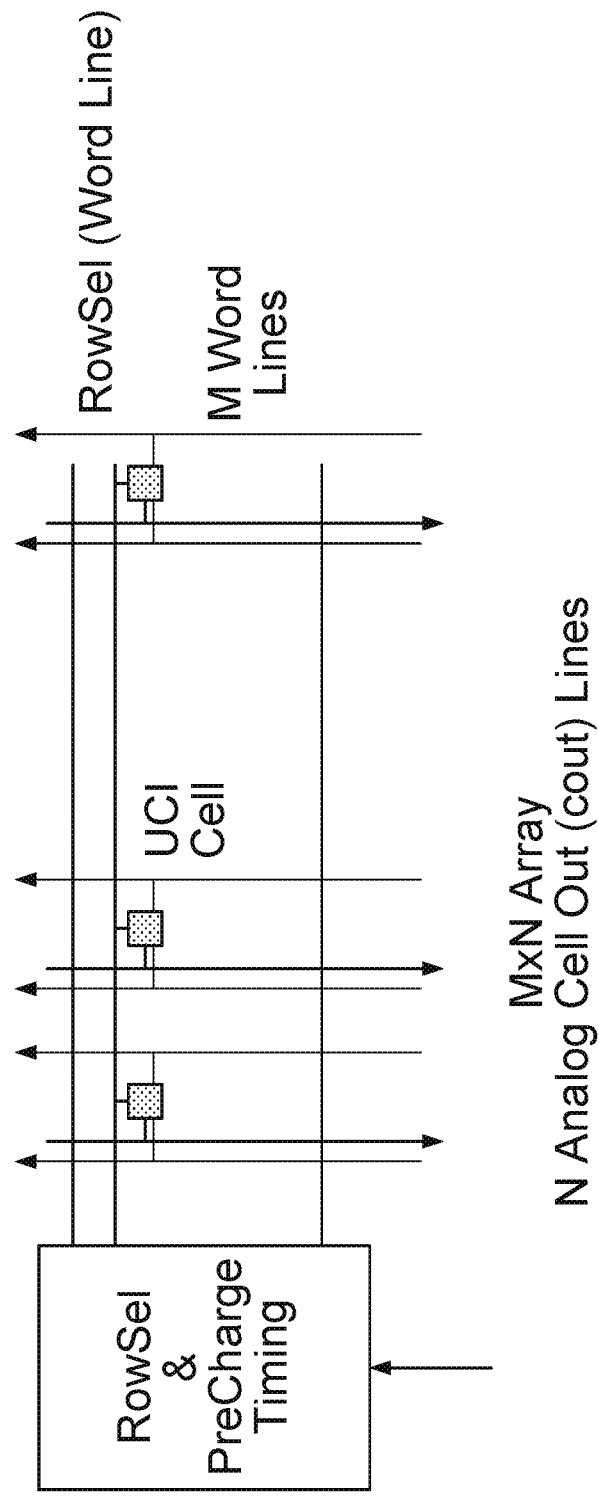
FIG. 7A illustrates an embodiment of an M×N bank of cells.

In some embodiments, the nanopore array is divided into banks of cells. FIG. 7A illustrates an embodiment of an M×N bank of cells. Row select and column select lines are used to control the states of the individual cells. M and N may be any integer numbers. For example, a bank that is 8 k in size (referred to as a bank8k) may include 64×128 cells.

Figure 7B:
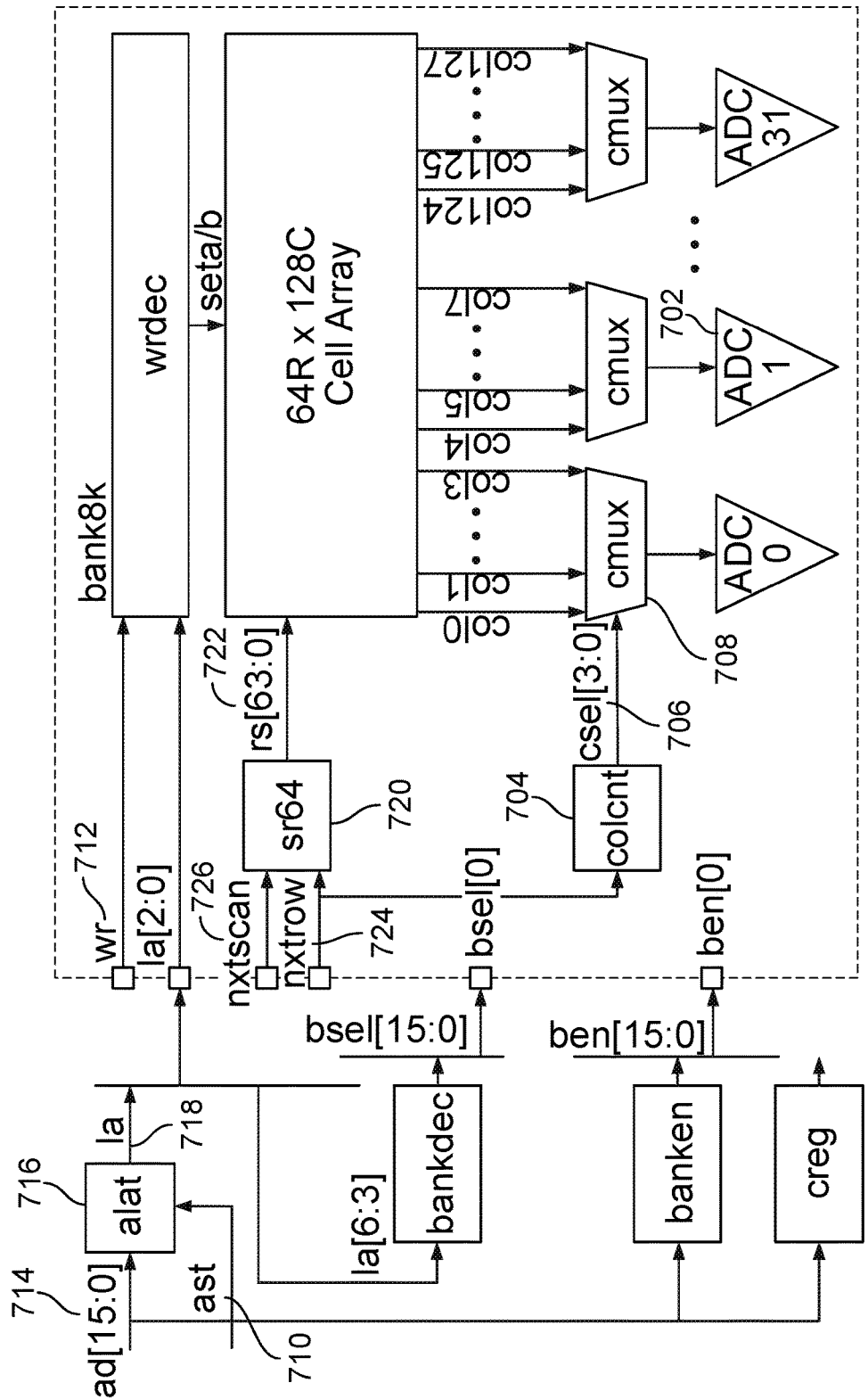
FIG. 7B illustrates an embodiment of a bank8k block.

FIG. 7B illustrates an embodiment of a bank8 k block. The bank8k building block may be configured as 64 rows by 128 columns as shown in FIG. 7B. Each bank8k block can be a complete sub-system with row and column addressing logic for reading/scanning, write address decoders, analog-to-digital converters (ADCs), and double buffered output.

Since each bank is autonomous, the nanopore array can be scaled by adding additional banks. For example, a 128 k array can be implemented as sixteen bank8k elements. A 512 k array can be implemented as an 8×8 array of bank8k elements. In some embodiments, the nanopore array may be scaled to include millions of cells. A small global control block may be used to generate control signals to select the banks and to set the cell applied voltage.

In some embodiments, the read path and the write path of the bank8k block are separate and operate in a time multiplexed fashion. For example, a read is followed by a write.

Each row is scanned by performing an analog-to-digital conversion of all of the cells in the row. Subsequently, software may optionally write a value to any cells in the same row in order to update the state, thereby selecting between two different applied voltages.

Each bank8k block incorporates thirty two ADCs 702 with each ADC 702 connected to 4 columns. A column counter (colcnt) 704 generates a 4 bit column select bus (csel) 706. The csel bus 706 controls 32 separate 4:1 analog muxes 708 and selects which of the 4 columns is electrically connected to the ADCs 702. Note that the sequential cells read from a given row are physically located as col0, col4, ... col1, col5, ..., and so on. The data is striped across the array with 16 bits. Similarly, the 16 bit data is written to the cells as:

$d[0:7] \rightarrow \{col0, col16, \ldots, col112\}$ $d[8:15] \rightarrow \{col1, col17, \ldots, col113\}$ In scan mode, all banks that are enabled are read out in parallel.

In some embodiments, scanning of a row requires reading 16 columns, with each column requiring 16 clock cycles. Thus, all cells in a row are read in 256 clocks, or 2 μs at a 128 MHz clock rate. The precharge period occurs immediately after a row has been scanned and lasts for 2 μs.

The bank8k is fully synchronous with all signals captured on the rising edge of the clocks, including ast 710, wr 712, and multiplexed address data bus 714 (ad[15:0]). During the first clock cycle, ad[15:0] is driven with the write address which is captured by the address latch 716 (alat) on the rising edge of the clock when address strobe 710 (ast) signal is high. Seven latched address (la) 718 bits are decoded to determine to which bank and word data is written. During the second clock cycle, ad[15:0] should be driven with the data and the wr 712 signal should be asserted high to indicate that this is a data write cycle. Thus, a normal write requires two cycles: the address cycle (indicated by the ast 710 signal), followed by the data cycle (indicated by the wr 712 signal).

There are three types of writes:
Bank Enable Register Write
Control Register write
Bank Cell A/B Select Write Some of the bits of the latched address 718, la[8:7], are used to determine the type of write, as shown in Table 1 below:

TABLE 1

| la[8:7] | Type of Write |
|---------|---------------|
| 00 | Cell A/B Select |
| 01 | Bank Enable Register |
| 10 | Control Register |

The row select (rs) shift register 720 logic and the column counter 704 (colcnt) together operate to perform a raster scan of all the cells in the bank8k block. After a full integration period, a row is read out by asserting the row select 722 (rs) signal high. Together, the row select 722 and column select 704 enable a single cell to drive a given column. Eight columns within a row are read out in parallel, each connected to a different ADC. A selected cell drives the voltage on an integrating capacitor onto the column line using an in-cell source follower amplifier.

The row select logic is a 64 bit shift register (sr64 register 720) duplicated within every bank8k block. After all columns in a row have been read, an external FPGA (field-programmable gate array) may assert the nxtrow signal 724, which causes the sr64 register 720 to shift. Once the entire sub-windowed field has been scanned, the external FPGA asserts the nxtscan 726, which resets the sr64 register 720 back to row zero by shifting 1 bit into the first flip flop. By changing the period and the duration of the nxtrow 724 and nxtscan 726 signal, the array being scanned can be windowed, as will be described in greater detail below.

Precharging occurs on a row by row basis. A row goes into the precharge mode immediately after a row has been sampled by the ADCs. Each row has a flip flop that samples the row_enable signal when nxtrow 724 signal is asserted.

In addition, the row select shift register 720 is also used to generate the row precharge signal by connecting the nth precharge signal to the (n+1)th row select signal:

$Pre[n] = rs[n+1]$

A row is precharged during the row scanning period immediately after it has been read. This bit shifted precharge connection is implemented as a modulo 64 operation, and thus precharge[63] is logically connected to rs[0].

Figure 8:
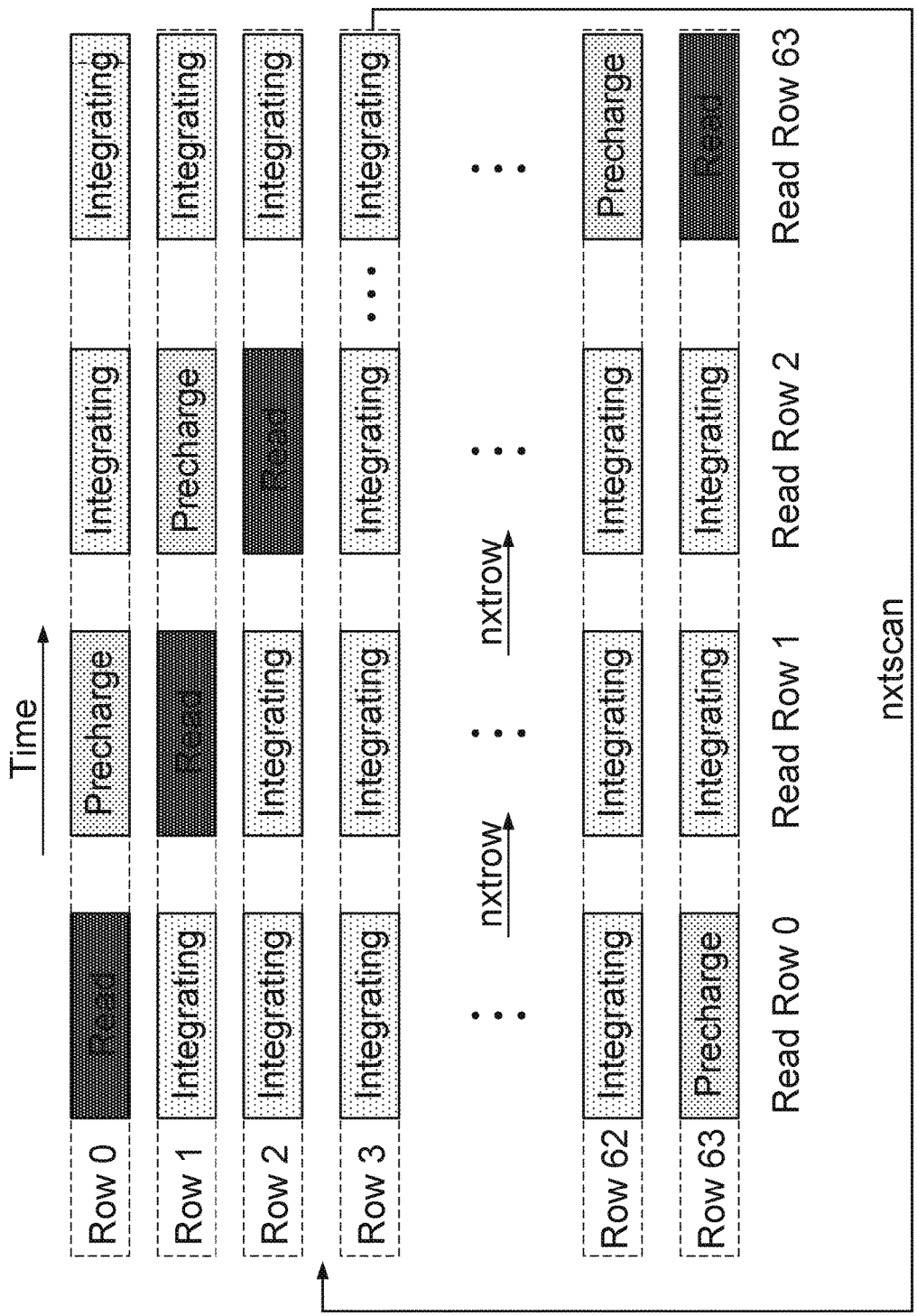
FIG. 8 illustrates an embodiment of a scan sequence.

FIG. 8 illustrates an embodiment of a scan sequence. After all 64 rows have been read (along with any intervening writes), the nxtscan signal is asserted to restart the scanning process at row 0.

Figure 9:
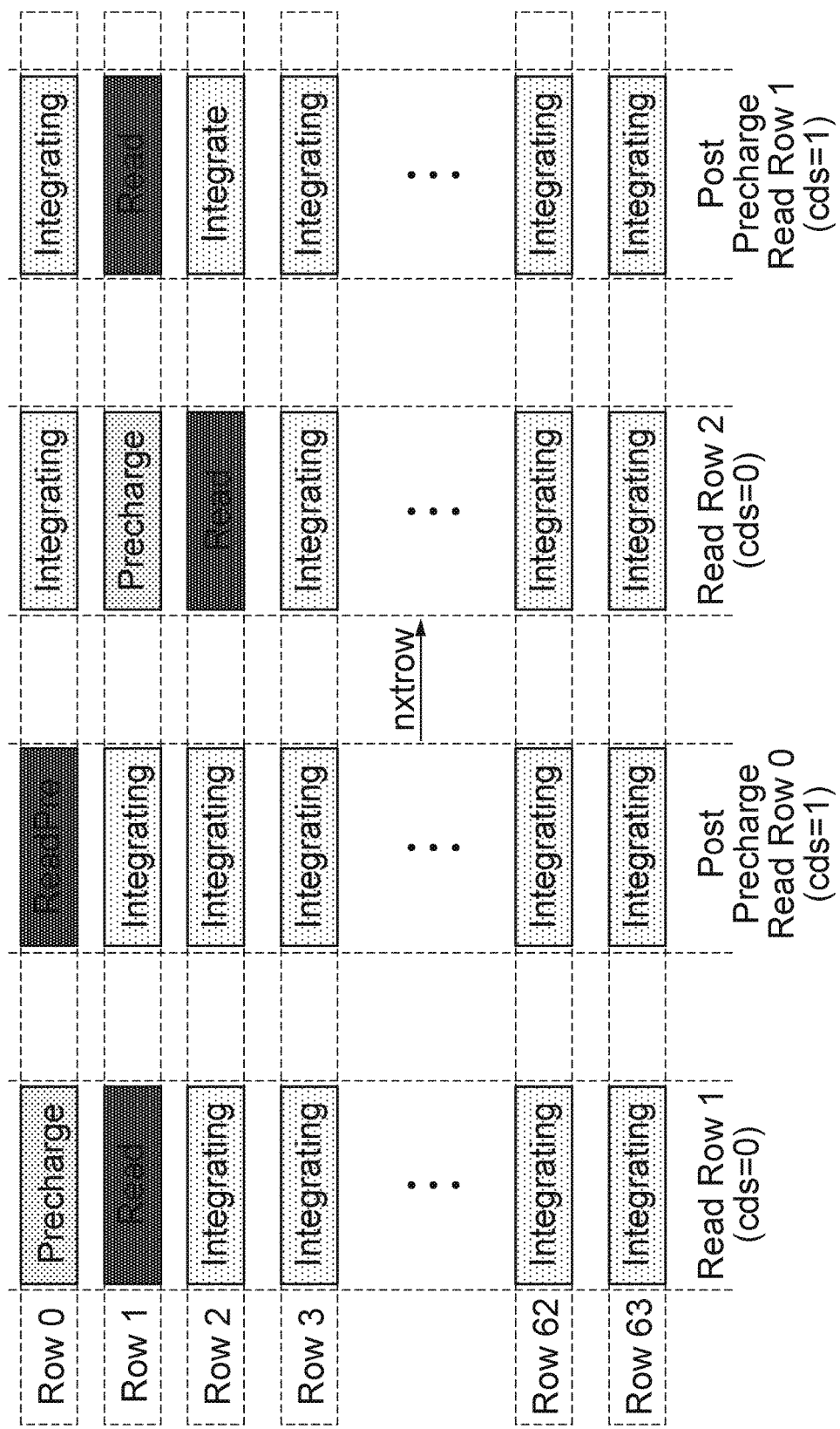
FIG. 9 illustrates an embodiment of a scan sequence.

FIG. 9 illustrates an embodiment of a scan sequence. Correlated double sampling (CDS) is enabled by asserting a CDS pin. In a normal measurement mode without CDS, the voltage on the capacitor is measured, and subsequently the nxtrow pin is asserted so that the next row can be read. Row N is pre-charged while Row N+1 is being read. Thus, a row is reset immediately after it has been read. Asserting the CDS pin allows the row that has just been precharged to be read. Thus, the value of the reset voltage can be read immediately after precharging is done and subsequently read again at a later time. By subtracting the two measurements, the kT/C thermal noise of the precharge transistor 1114 is reduced. In addition, charge sharing voltage divider effects between the integrator capacitance and the active follower in the cell are also reduced. Note that when correlated double sampling is performed, the effective measurement rate is reduced by half, since two ADC conversions are required for each integrated current measurement.

The row and column addresses are controlled by the nxtrow 724 and nxtscan 726 signals. Asserting the nxtrow 724 input high causes the column address and the shift register to be reset to 0 and the row address to be shifted by one. Asserting the nxtscan 726 input high causes the row and column addresses to be reset to 0.

In a normal operation, the entire 8K cell array within each bank is scanned. The ADC requires 16 clock cycles to perform a conversion, and 16 such conversions are performed in order to convert an entire row. Thus, each row requires 256 clock cycles (2.0 μs @ 128 MHz).

Figure 10:
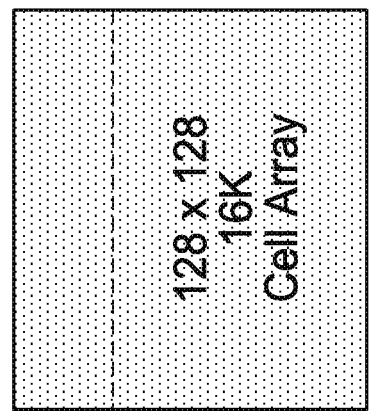
FIG. 10 illustrates an embodiment wherein a fraction of the array may be scanned at a time.

Thus, in order to scan the entire 8K cell array, the nxtrow 724 signal is asserted every 256 cycles and the nxtscan 726 signal is asserted for one cycle in every 16,384 cycles. Using a typical clock running at 128 MHz yields a sample rate of 7.8 kHz (128 is period). It is however possible to tradeoff the number of scanned cells for a higher scan rate by scanning a subset of the array. For example, the top one-quarter of rows of the array may be scanned by asserting the nxtscan 726 signal after 2048 clocks, as shown in FIG. 10. The sampling rate is increased by four times, from ~8 kHz to ~32 kHz. However, the integration time and the voltage signal are reduced by 4 times as well, causing degradation of the signal-to-noise ratio (SNR).

In the above example, one quarter of the array is scanned. However, a larger or a smaller fraction of the array may be scanned at a time. For example, ½ or ⅓ of the rows of the full array may be scanned at a time.

In the above example, three-quarters of the array is left unscanned. In some embodiments, the entire array is scanned in multiple passes. The first pass is as described above. The second pass leaves the nxtrow 724 signal asserted for 16 consecutive clock cycles to bypass the first 16 rows and start a new scan on the 17th. Scanning of the next quarter of the array is then performed normally before asserting the nxtscan 726 to reset the scan shift registers. The third quarter skips 32 rows and starts scanning on the 33rd to scan the final 16 rows.

Thus, by time-interleaving, the entire array is scanned at a much higher rate than normal. The actual sample rate is not improved, since the time required to scan all four quarters of the array does not change. There are effectively "dead times" inserted between each of the quartile scans. In some cases, the current is such that the voltage measurement saturates at the normal 8 kHz scanning rate. Thus, by time-interleaving faster scans, readings of these high current cells in the array are obtained without saturating. The software needs to be cognizant of the precharge signal and perform a double scan of the desired region.

In each cell, current is measured at different applied voltages. The cell includes a circuitry to apply a constant voltage (DC voltage) or an alternating voltage waveform (AC voltage) to the electrode and measure a low level current simultaneously.

In some embodiments, a voltage potential is applied to the liquid contained within a conductive cylinder mounted to the surface of the die. This "liquid" potential is applied to the top side of the pore and is common to all cells in the array. The bottom side of the pore has an exposed electrode, and each sensor cell can apply a distinct bottom side potential to its electrode. The current is measured between the top liquid connection and each cell's electrode connection on the bottom side of the pore. The sensor cell measures the current travelling through the pore as modulated by the molecular complex constricted within the pore.

Figure 11:
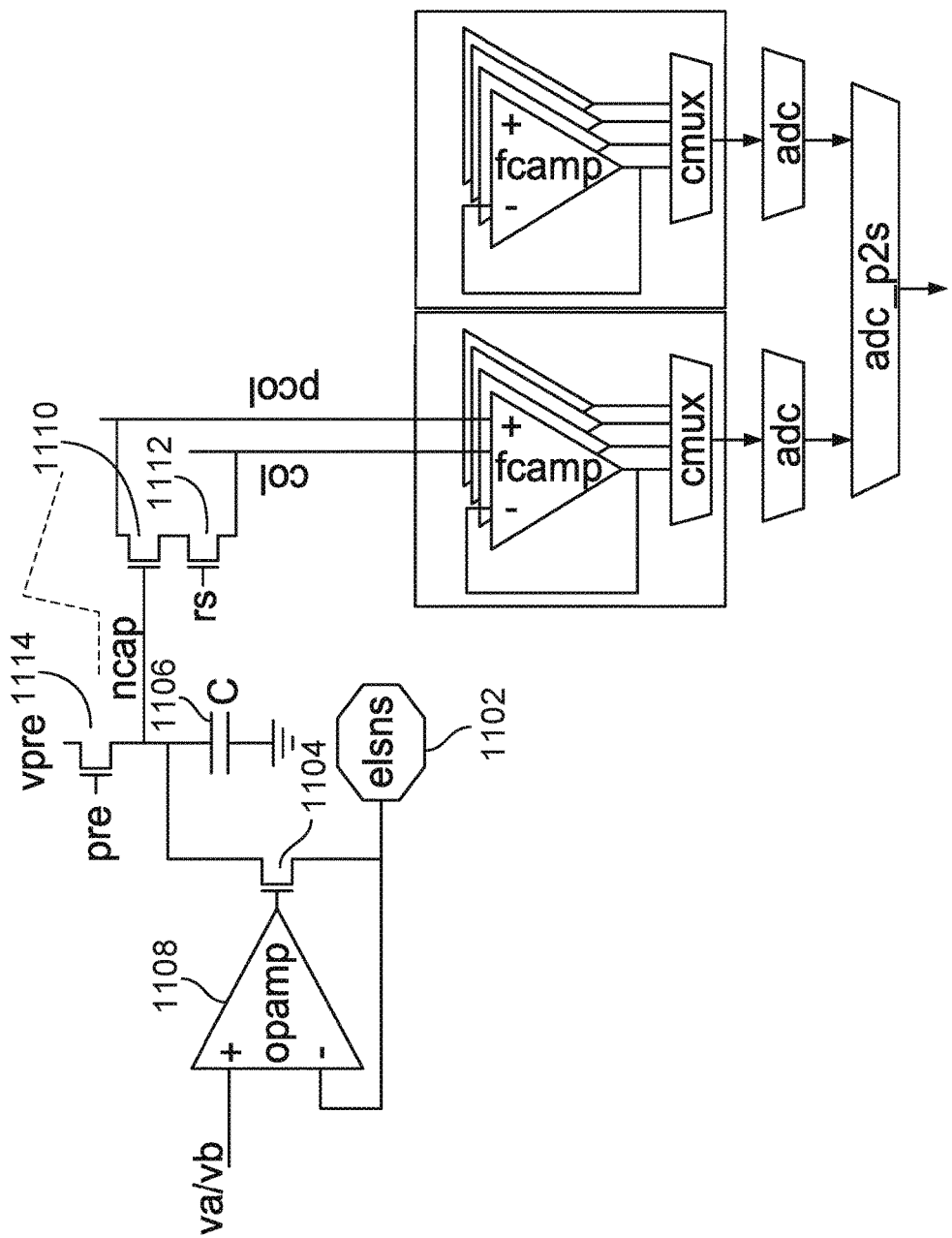
FIG. 11 illustrates an embodiment of an analog circuit for measuring the current in a cell.

FIG. 11 illustrates an embodiment of an analog circuit for measuring the current in a cell. The circuit is electrically connected to an electrochemically active electrode (e.g., AgCl) through an electrode-sense (ELSNS) node 1102. The circuit includes a transistor 1104. Transistor 1104 may be an NMOS or n-channel MOSFET (metal-oxide-semiconductor field-effect transistor) that performs two functions. A controlled voltage potential can be applied to ELSNS node 1102, and the controlled voltage potential can be varied by changing the voltage on the input to an op-amp 1108 controlling transistor 1104, which acts as a source follower. Transistor 1104 also operates as a current conveyer to move electrons from a capacitor 1106 to ELSNS node 1102 (and vice versa). Current from the source pin of transistor 1104 is directly and accurately propagated to its drain pin, accumulating charges on capacitor 1106. Thus, transistor 1104 and capacitor 1106 act together as an ultra-compact integrator (UCI).

The UCI is used to determine the current sourced from or sunk to the electrode by measuring the change in voltage integrated onto capacitor 1106 according to the following:

$$I*t = C*\Delta V$$

where, I: Current
t: integration time
C: Capacitance
ΔV: voltage change

Typical operation involves precharging capacitor 1106 to a known and fixed value (e.g., VDD=1.8 V), and then measuring the voltage change at a fixed interval t. For an 8K bank operating at 128 MHz, each cell integrates for ~128 μs. In one example:

$$C = 5fF$$
$$I = 20\text{pA}$$
$$t = 128\mu s$$
$$\Delta V = I*t/C$$
$$= 20\text{pA}*128\mu s/5fF$$
$$= 512\text{mV}$$

In this example the resolution of the ADC is on the order of millivolts. The integrated voltage may be increased by reducing the clock rate to less than 128 MHz, thereby increasing the integration period.

In the above circuit, the maximum voltage swing is ~1V, and thus the circuit saturates with a current higher than ~32 pA. The saturation limit can be increased by reducing the scan window to effectively increase the cell scan rate. By interleaving fast and slow scans, the dynamic range of the current that can be measured can be increased.

Transistor 1104 acts as a current conveyor by moving charges from the integrating capacitor 1106 to the electrode. Transistor 1104 also acts as a voltage source, imposing a constant voltage on the electrode through the opamp feedback loop. The column drive transistor 1110 is configured as a source follower in order to buffer the capacitor voltage and provide a low impedance representation of the integrated voltage. This prevents charge sharing from changing the voltage on the capacitor.

Transistor 1112 is a transistor connected to the row select (rs) signal. It is used as a row access device with the analog voltage output at its source connected as a column shared with many other cells. Only a single row of the column connected AOUT signal is enabled so that a single cell voltage is measured.

In an alternative embodiment, the row select transistor (transistor 1112) may be omitted by connecting the drain of the column drive transistor 1110 to a row selectable "switched rail."

A precharge transistor 1114 is used to reset the cell to a predetermined starting voltage from which the voltage is integrated. For example, applying a high voltage (e.g., VDD=1.8 V) to both vpre and pre will pull capacitor 1106 up to a precharged value of (VDD−Vt). The exact starting value can vary both from cell to cell (due to Vt variation of precharge transistor 1114) as well as from measurement to measurement, due to the reset switch thermal noise (sqrt (kTC) noise). It is possible to eliminate this Vt variation by limiting the precharge voltage to less than VDD−Vt. In this case, the precharge transistor 1114 will pull all the way up to the vpre voltage. Even in this case, however, the kT/C noise is still present. As a result, a correlated double sampling (CDS) technique is used to measure the integrator starting voltage and the ending voltage to determine the actual voltage change during the integration period. CDS is accomplished by measuring the voltage on the integrating capacitor 1106 twice: once at the beginning and once at the end of the measurement cycle.

Note also that the drain of precharge transistor 1114 is connected to a controlled voltage vpre (reset voltage). In a normal operation, vpre is driven to a fixed voltage above the electrode voltage. However, it can also be driven to a low voltage. If the vpre node of precharge transistor 1114 is in fact driven to ground, then the current flow is reversed (i.e., current flows from the electrode into the circuit through transistor 1104 and precharge transistor 1114), and the notion of source and drain is swapped. The negative voltage applied to the electrode (with respect to the liquid reference) is controlled by the vpre voltage, assuming that the gate voltages of transistors 1114 and 1104 are at least greater than vpre by a threshold. Thus, a ground voltage on vpre can be used to apply a negative voltage to the electrode, for example to accomplish electroporation or bilayer formation.

An ADC measures the AOUT voltage immediately after reset and again after the integration period (i.e., performs the CDS measurement) in order to determine the current integrated during a fixed period of time. An ADC can be implemented per column. A separate transistor may be used for each column as an analog mux to share a single ADC between multiple columns. The column mux factor can be varied depending on the requirements for noise, accuracy, and throughput.

Figure 12:
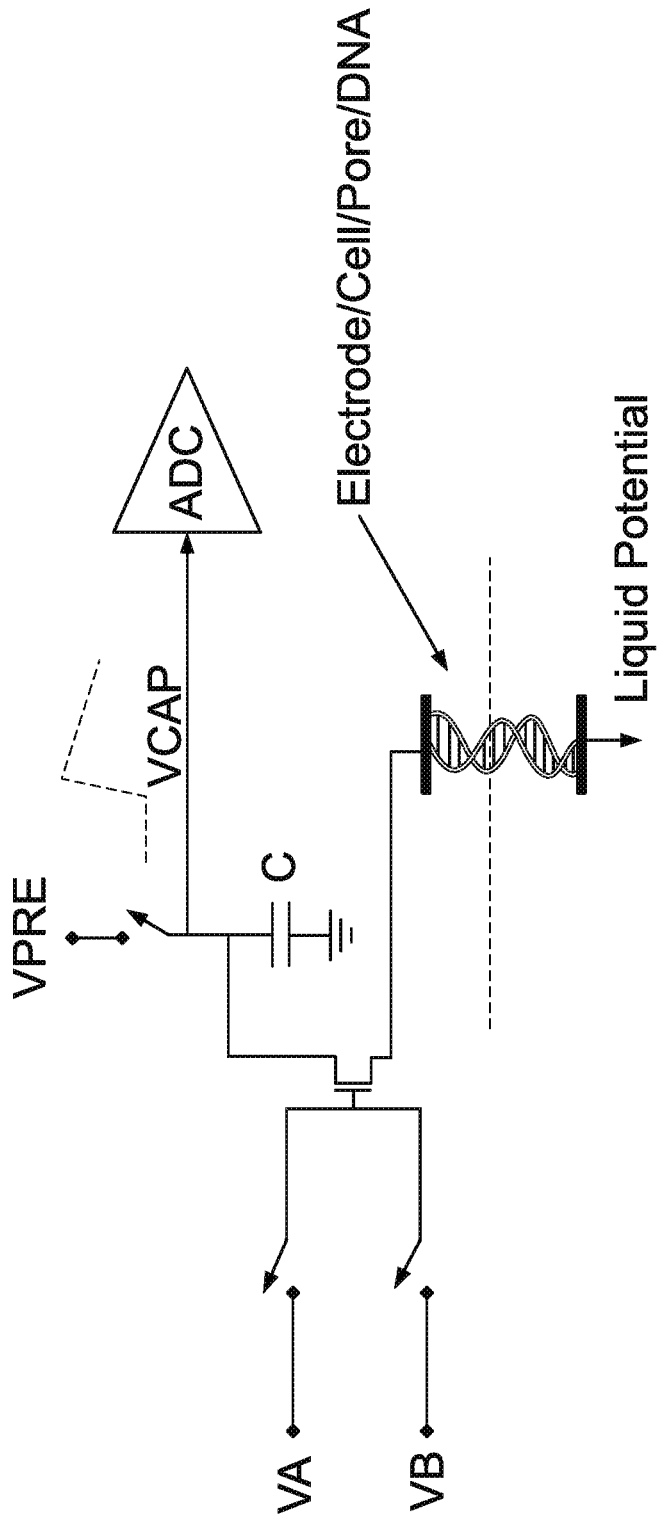
FIG. 12 illustrates an embodiment of an analog circuit for measuring the current in a cell.

In some alternative embodiments, the op-amp/transistor combination as shown in FIG. 11 may be replaced by a single transistor as shown in FIG. 12.

In some embodiments, vias may be placed within a cell or within a group of cells. Placing a via within a cell or within a group of cells is referred to as cell-level stacking Cell-level stacking may be used when a via has a cross-sectional area that is small relative to the cell or groups of cells in which the via is placed. For example, a via used in cell-level stacking may have a diameter of 1 µm.

In FIG. 5A, FIG. 5B, and FIG. 6, each of the stacked-wafers nanopore-based sequencing chip (500 and 600) has two wafers. However, in some other embodiments, a stacked-wafer nanopore-based sequencing chip may have two or more wafers that are stacked vertically together.

In one embodiment, a stacked-wafers nanopore based sequencing chip includes three wafers. The memory components and logic components are located on the bottom wafer. The cell array is divided between the top and middle wafers; for example, analog measurement circuitry 112 (see FIG. 1) of cell 100 is placed on the middle wafer, while the remaining components of cell 100 are placed on the top wafer.

In one embodiment, a stacked-wafers nanopore based sequencing chip includes three wafers. The top wafer includes the cell array and the analog components. A middle wafer includes the memory components. A bottom wafer includes the logic components. In this embodiment, the memory components and the logic components are located on separate wafers such that each wafer may be designed using different types of technologies. Cell-level stacking may be used such that a via delivers signals between wafers. Suppose an analog output signal from a cell needs to be compared to a value, and a decision needs to be made based on the comparison. The analog output signal is routed to a comparator located on the top wafer. A via delivers a value stored in a memory component corresponding to the cell to the comparator, such that a comparison of the analog output signal and the stored value can be made. The result of the comparison may be further delivered by a via to the logic components located on the bottom wafer, where a decision can be made. In some embodiments, a logic component may be shared by multiple cells. For example, comparison results from four different cells may be delivered by a single via to the shared logic component, where detections/decisions are made.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A nanopore based sequencing chip, comprising:
 a first portion made from a first wafer, the first portion comprising:
   an array of nanopore cells;
   a measurement circuit connected to one or more nanopore cells, the measurement circuit producing an output measurement signal corresponding to the one or more nanopore cells; and
   one or more vias transmitting the output measurement signal corresponding to the one or more nanopore cells; and
   one or more vias receiving control signal for controlling the one or more nanopore cells; and
 a second portion made from a second wafer, wherein the first wafer and the second wafer are stacked vertically on top of one another within the same nanopore based sequencing chip wherein the first portion made from the first wafer includes only analog components and wherein the second portion made from the second wafer includes only digital components and wherein the second portion comprising:
   one or more vias receiving the output measurement signal corresponding to the one or more nanopore cells transmitted from the one or more vias in the first portion made from the first wafer;
   a module generating the control signal in response to a detected event based on the output measurement signal corresponding to the one or more nanopore cells that is transmitted from the one or more vias in the first portion made from the first wafer; and
   one or more vias transmitting the control signal to the one or more vias in the first portion made from the first wafer that is receiving the control signal for controlling the one or more nanopore cells, such that the control signal is further routed by a circuitry in the first portion made from the first wafer to the one or more nanopore cells.

2. The nanopore based sequencing chip of claim 1, wherein the one or more vias transmitting the output measurement signal, the one or more vias receiving the control signal, the one or more vias receiving the output measurement signal, and the one or more vias transmitting the control signal are located at the periphery of the nanopore based sequencing chip.

3. The nanopore based sequencing chip of claim 1, wherein the one or more vias transmitting the output measurement signal corresponding to the one or more nanopore cells in the first portion made from the first wafer are located within a single nanopore cell.

4. The nanopore based sequencing chip of claim 1, wherein the one or more vias transmitting the output measurement signal corresponding to the one or more nanopore cells in the first portion made from the first wafer are located within a group of nanopore cells that share one or more components located in the second portion made from the second wafer, and wherein the one or more vias transmitting the output measurement signal corresponding to the one or more nanopore cells in the first portion made from the first wafer transmit the output measurement signal to the one or more shared components in the second portion made from the second wafer.

5. The nanopore based sequencing chip of claim 1, wherein the second portion made from the second wafer further comprises a module compressing the output measurement signal corresponding to the one or more nanopore cells in the first portion made from the first wafer.

6. The nanopore based sequencing chip of claim 1, wherein the first portion made from the first wafer further comprises an analog-to-digital converter (ADC) converting the output measurement signal to a digital version of the output measurement signal prior to the transmission of the digital version of the output measurement signal by the one or more vias transmitting the output measurement signal corresponding to the one or more nanopore cells in the first portion made from the first wafer.

7. A method of performing nucleotide sequencing by a nanopore based sequencing chip, comprising:
 partitioning the nanopore based sequencing chip into a first portion made from a first wafer, the first portion comprising:
  an array of nanopore cells;
  a measurement circuit connected to one or more nanopore cells, the measurement circuit producing an output measurement signal corresponding to the one or more nanopore cells; and
  one or more vias transmitting the output measurement signal corresponding to the one or more nanopore cells; and
  one or more vias receiving control signal for controlling the one or more nanopore cells; and
 partitioning the nanopore based sequencing chip into a second portion made from a second wafer, wherein the first wafer and the second wafer are stacked vertically on top of one another within the same nanopore based sequencing chip wherein the first portion made from the first wafer includes only analog components and wherein the second portion made from the second wafer includes only digital components and wherein the second portion comprising:
  one or more vias receiving the output measurement signal corresponding to the one or more nanopore cells transmitted from the one or more vias in the first portion made from the first wafer;
  a module generating the control signal in response to a detected event based on the output measurement signal corresponding to the one or more nanopore cells transmitted from the one or more vias in the first portion made from the first wafer; and
  one or more vias transmitting the control signal to the one or more vias in the first portion made from the first wafer receiving the control signal for controlling the one or more nanopore cells, such that the control signal is further routed by a circuitry in the first portion made from the first wafer to the one or more nanopore cells.

8. The method of claim 7, wherein the one or more vias transmitting the output measurement signal, the one or more vias receiving the control signal, the one or more vias receiving the output measurement signal, and the one or more vias transmitting the control signal are located at the periphery of the nanopore based sequencing chip.

9. The method of claim 7, wherein the one or more vias transmitting the output measurement signal corresponding to the one or more nanopore cells in the first portion made from the first wafer are located within a single nanopore cell.

10. The method of claim 7, wherein the one or more vias transmitting the output measurement signal corresponding to the one or more nanopore cells in the first portion made from first wafer are located within a group of nanopore cells that share one or more components located in the second portion made from the second wafer, and wherein the one or more vias transmitting the output measurement signal corresponding to the one or more nanopore cells in the first portion of the first wafer transmit the output measurement signal to the one or more shared components on the second portion made from the second wafer.

11. The method of claim 7, wherein the second portion made from the second wafer further comprises a module compressing the output measurement signal corresponding to the one or more nanopore cells in the first portion made from the first wafer.

12. The method of claim 7, wherein the first portion made from the first wafer further comprises an analog-to-digital converter (ADC) converting the output measurement signal to a digital version of the output measurement signal prior to the transmission of the digital version of the output measurement signal by the one or more vias transmitting the output measurement signal corresponding to the one or more nanopore cells in the first portion made from the first wafer.

\* \* \* \* \*

UNITED STATES PATENT AND TRADEMARK OFFICE
CERTIFICATE OF CORRECTION

PATENT NO. : 10,006,899 B2
APPLICATION NO. : 14/225263
DATED : June 26, 2018
INVENTOR(S) : Tian Page 1 of 1

It is certified that error appears in the above-identified patent and that said Letters Patent is hereby corrected as shown below:

In Column 06, Line 51, delete "bank8 k" and insert --bank8k--, therefor.

In Column 08, Line 62, delete "128 is" and insert --128 μs--, therefor.

Signed and Sealed this
Fourth Day of December, 2018

Andrei Iancu
*Director of the United States Patent and Trademark Office*